US009283067B2

(12) United States Patent
Da Cruz Louro

(10) Patent No.: US 9,283,067 B2
(45) Date of Patent: Mar. 15, 2016

(54) PROSTHESIS FOR CONNECTING AN ANATOMICAL DUCT

(75) Inventor: Pierre Da Cruz Louro, Villabe (FR)

(73) Assignee: CARMAT, Vélizy Villacoublay (FR)

( * ) Notice: Subject to any disclaimer, the term of this patent is extended or adjusted under 35 U.S.C. 154(b) by 249 days.

(21) Appl. No.: 14/006,570

(22) PCT Filed: Mar. 5, 2012

(86) PCT No.: PCT/FR2012/050449
§ 371 (c)(1),
(2), (4) Date: Sep. 20, 2013

(87) PCT Pub. No.: WO2012/127145
PCT Pub. Date: Sep. 27, 2012

(65) Prior Publication Data
US 2014/0012179 A1    Jan. 9, 2014

(30) Foreign Application Priority Data
Mar. 22, 2011  (FR) ...................... 11 52364

(51) Int. Cl.
*A61B 19/00* (2006.01)
*A61F 2/06* (2013.01)
*A61B 17/11* (2006.01)
*A61M 1/10* (2006.01)

(52) U.S. Cl.
CPC . *A61F 2/06* (2013.01); *A61B 17/11* (2013.01); *A61F 2/064* (2013.01); *A61M 1/1008* (2014.02); *A61B 2017/1107* (2013.01); *A61B 2017/1132* (2013.01)

(58) Field of Classification Search
CPC ............... A61M 39/1011; A61M 39/1033; A61M 1/1008; A61M 2001/1008; A61M 2039/1066; A61F 2/064; A61B 2017/1107; A61B 2017/1132
See application file for complete search history.

(56) References Cited

U.S. PATENT DOCUMENTS

| 8,088,117 | B2* | 1/2012 | Stephens et al. ............. 604/411 |
| 2002/0095210 | A1* | 7/2002 | Finnegan et al. ............ 623/3.26 |
| 2004/0054405 | A1 | 3/2004 | Richard |
| 2004/0087986 | A1* | 5/2004 | Ott ................................. 606/153 |
| 2010/0036397 | A1 | 2/2010 | Kang |
| 2012/0109168 | A1 | 5/2012 | Gerhardt |

FOREIGN PATENT DOCUMENTS

| WO | 00/24339 | 5/2000 |
| WO | 03/086528 | 10/2003 |
| WO | 04/001272 | 12/2003 |
| WO | 2010/022705 | 3/2010 |

OTHER PUBLICATIONS

International Search Report dated May 3, 2012.

* cited by examiner

*Primary Examiner* — Leslie Deak
(74) *Attorney, Agent, or Firm* — Dickinson Wright PLLC

(57) ABSTRACT

According to the invention, the tubular prosthesis for connecting an anatomical duct includes at least two individual tubular elements and a sealed mechanical element for connecting said separate elements to each other.

10 Claims, 4 Drawing Sheets

PROSTHESIS FOR CONNECTING AN ANATOMICAL DUCT

The present invention relates to a prosthesis for connecting an anatomical duct.

Although it is particularly suitable for connecting two portions of the same anatomical duct (for example, a blood vessel), the prosthesis according to the present invention can also be used to connect an anatomical duct to an organ or to an artificial device (for example a cardiac prosthesis or a ventricular assist device).

Moreover, it is known that some diseases or medical disorders require the removal of a portion of a blood vessel (for example an artery or a vein) for replacement by a vascular prosthesis. This type of prosthesis comprises, for example, a monolithic tubular body forming an anatomical duct over its entire length, generally cylindrical in form.

For implanting a vascular prosthesis of the above-mentioned type it is also known that surgical teams must cut the diseased portion of the vessel and then suture each of the free portions of the vessel thus out to an end of the monolithic vascular prosthesis.

However, because some vessels are difficult to access and/or because suturing a prosthesis to a vessel is difficult to perform, surgeons are obliged to cut the vascular prosthesis in two in order to facilitate the suturing of the ends of said prosthesis to the vessel to be treated. Once this has been performed, surgeons suture the two free ends of the prosthesis to each other.

In other words, this type of vascular prosthesis requires a supplementary suture zone (the zone defined between the two out ends of the prosthesis), which increases the time needed to implant the prosthesis and the haemodynamic risks (for example, stasis, haemorrhaging through the suture stitches made, etc.).

Drawbacks of this type are also observed when connecting a blood vessel to a cardiac prosthesis by means of a monolithic vascular prosthesis of the above-mentioned type.

The object of the present invention is to overcome these drawbacks.

Therefore, according to the invention, the tubular prosthesis for connecting an anatomical duct, which comprises at least two individual tubular elements and mechanical means for connecting said individual elements to each other, is notable in that the mechanical connecting means are sealed and comprise:
two annulus-shaped joining parts, each of them being fixed to the free end of an individual tubular element;
at least one seal (for example, taking the form of a preformed compressible mechanical seal or alternatively GRF (gelatine-resorcinol-formaldehyde) surgical glue applied to one of the two joining parts and designed to be inserted between the two joining parts around the opening formed by the tubular prosthesis; and
a first and a second fixing ring each traversed by an individual tubular element and designed to cooperate with each other to hold together, one against the other, the two joining parts between which the seal is compressed.

Therefore, owing to the invention, it is no longer necessary to out the prosthesis, as it consists of at least two individual tubular elements, which ensures a clean and regular cutting zone. In addition, the mechanical connecting means fitted on the prosthesis allow the two free ends of the individual elements to be joined together quickly and easily without carrying out additional suturing. Consequently, the haemodynamic risks are substantially reduced and the work of the surgeons is made significantly easier.

In addition, the first and second fixing rings hold the joining parts firmly against each other and compress the seal between said rings, which helps guarantee the seal along the tubular prosthesis (in particular at the junction of the two parts). Bodily fluid (for example blood when the anatomical duct is a blood vessel) flowing into the prosthesis is also prevented from coming into contact with materials other than that of the individual tubular elements (which are preferably made of a biocompatible material, such as a woven polyester).

In an embodiment according to the invention:
the first fixing ring comprises an inner flange on which one of the annuluses is designed to be firmly pressed;
the second fixing ring comprises a projecting annular collar at the end of which the other annulus is positively connected; and
the projecting collar is suitable for being inserted inside the first ring in order to put the two annuluses in contact with each other.

In addition, according to this embodiment:
the first fixing ring may comprise internal radial projections; and
the second fixing ring may comprise recesses made in the side wall of the projecting collar and which are suitable for receiving the corresponding radial projections of the first ring.

Moreover, each of the radial projections may be in the form of a stud and each of the recesses may comprise:
an axial notch for the insertion of a radial projection; and
a locking incline extending over a particular, angular sector, the entrance of which is formed by the associated axial notch.

In particular, the locking incline may be helical and end in a locking notch, which allows the seal to be compressed in a predetermined manner and held in the locked position.

Furthermore, the radial projections and the corresponding recesses, preferably three in number, can be distributed at equal angles in order to maintain a uniform compression of the seal over its length.

In a variant embodiment according to the invention, the inner side wall of the first ring has threading suitable for cooperating with corresponding threading made in the outer side wall of the fixing collar. In addition, the first ring, mounted rotating freely around the corresponding individual tubular element is independent of the annulus associated therewith.

Moreover, the prosthesis advantageously comprises auxiliary fixing means for holding said annuluses securely against each other.

In particular, these auxiliary fixing means may comprise at least one fixing eyelet positively connected to the first fixing ring, and at least one corresponding fixing orifice made in the side wall of the second fixing ring, the fixing eyelet and the fixing orifice being suitable for being connected to each other, for example by a suture thread.

Moreover, it will be noted that, depending on the shape of the anatomical duct, the prosthesis may have a generally cylindrical, conical, bifurcated (if the anatomical duct is itself bifurcated) or other shape.

The figures of the accompanying drawings will make clear how the invention can be produced. In these figures, identical references refer to like elements.

As mentioned above, the prosthesis according to the present invention can be used just as well for connecting two portions of the same anatomical duct (for example a blood vessel) as for connecting an anatomical duct to an organ or to an artificial device (for example an artificial heart).

For reasons of clarity and conciseness, the prosthesis according to the invention will be described below in relation more particularly to blood vessels.

Figure 1:
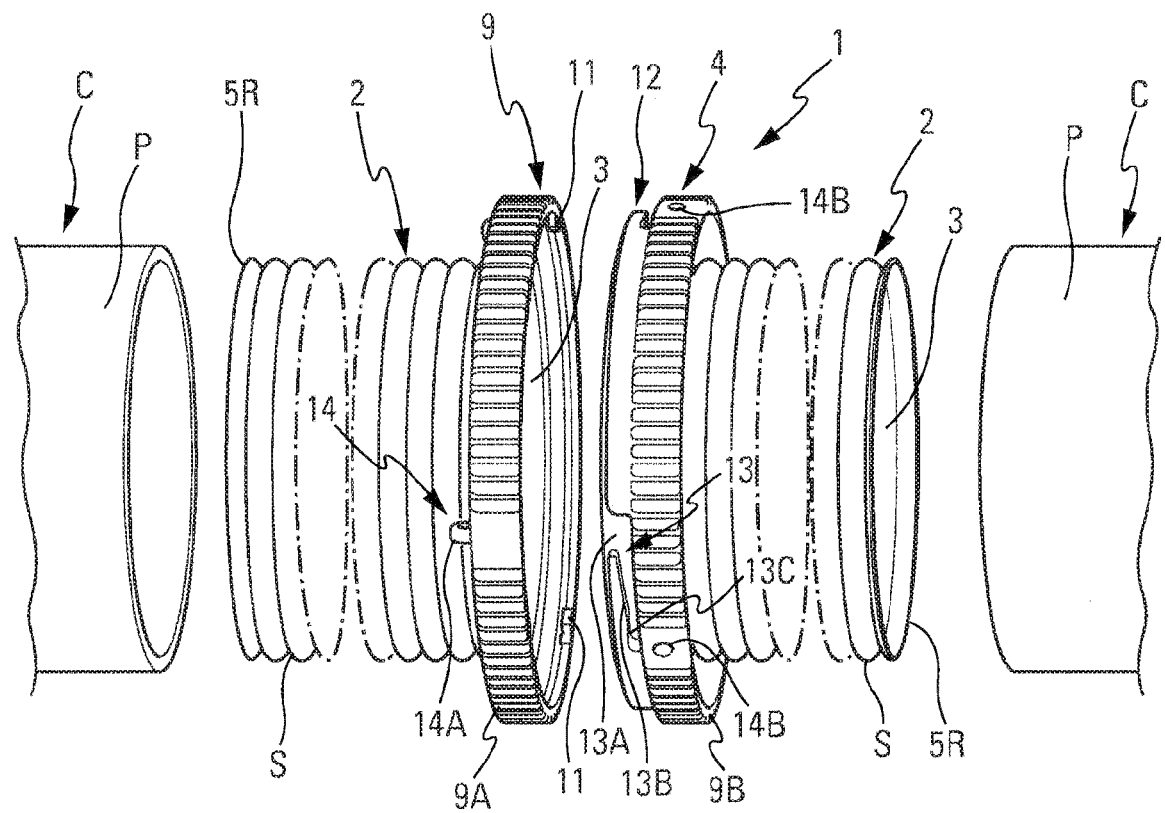
FIG. 1 shows diagrammatically in a perspective view, an embodiment of the prosthesis according to the present invention, in which the two individual tubular elements are not connected to each other.
Figure 2:
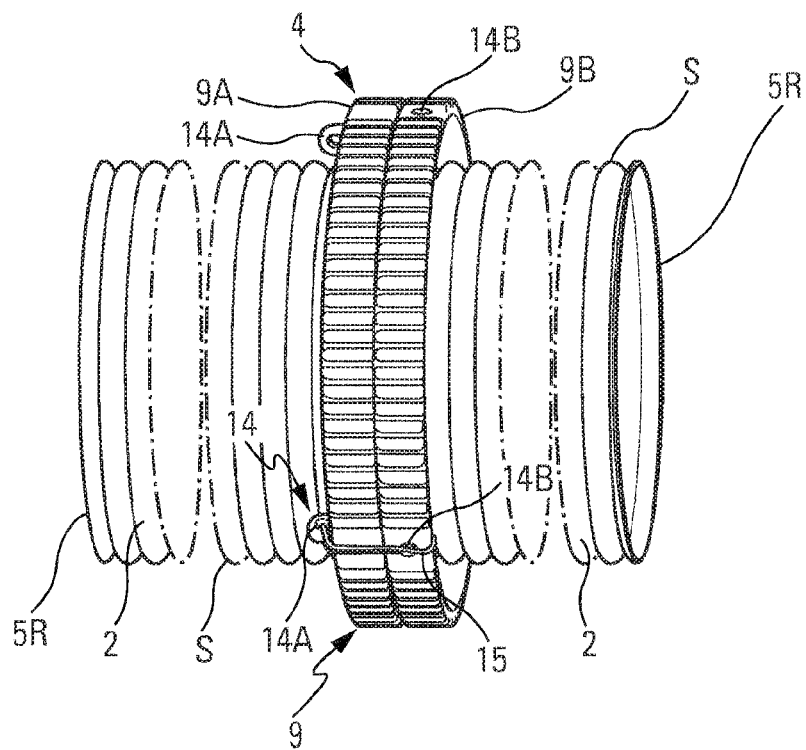
FIG. 2 is similar to FIG. 1 except that the two individual tubular elements of the prosthesis are connected to each other.
Figures 3, 4:
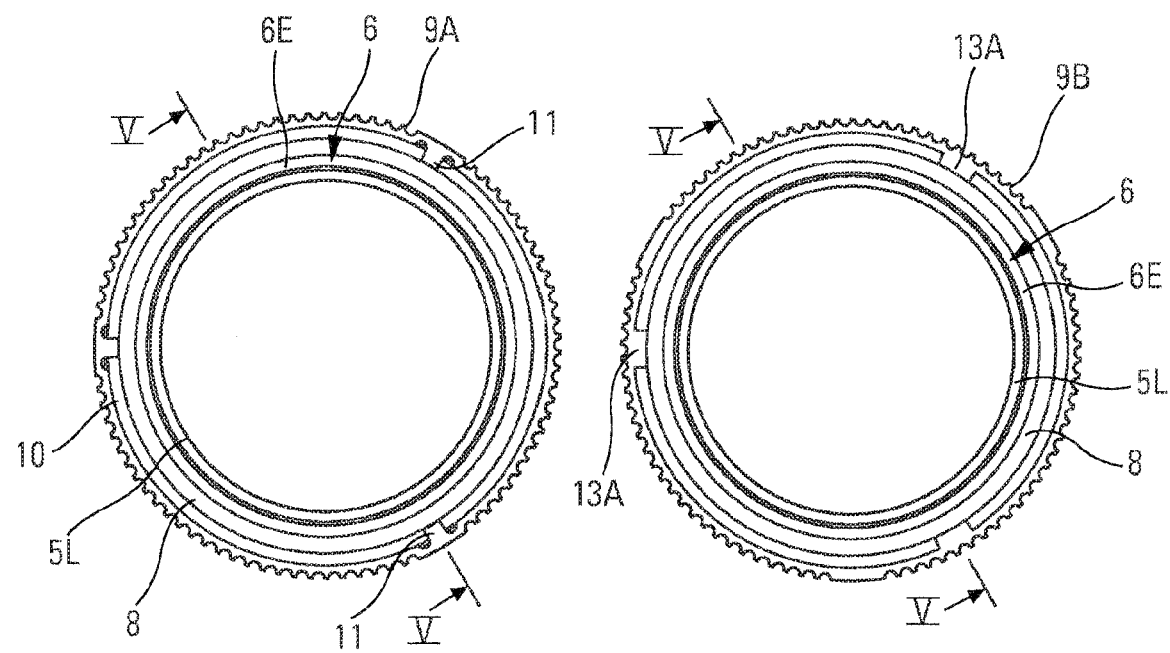
FIGS. 3 and 4 are diagrammatic views from the front of a free end of an individual tubular element comprising the first fixing ring (FIG. 3) and the second fixing ring (FIG. 4) respectively.
Figure 5:
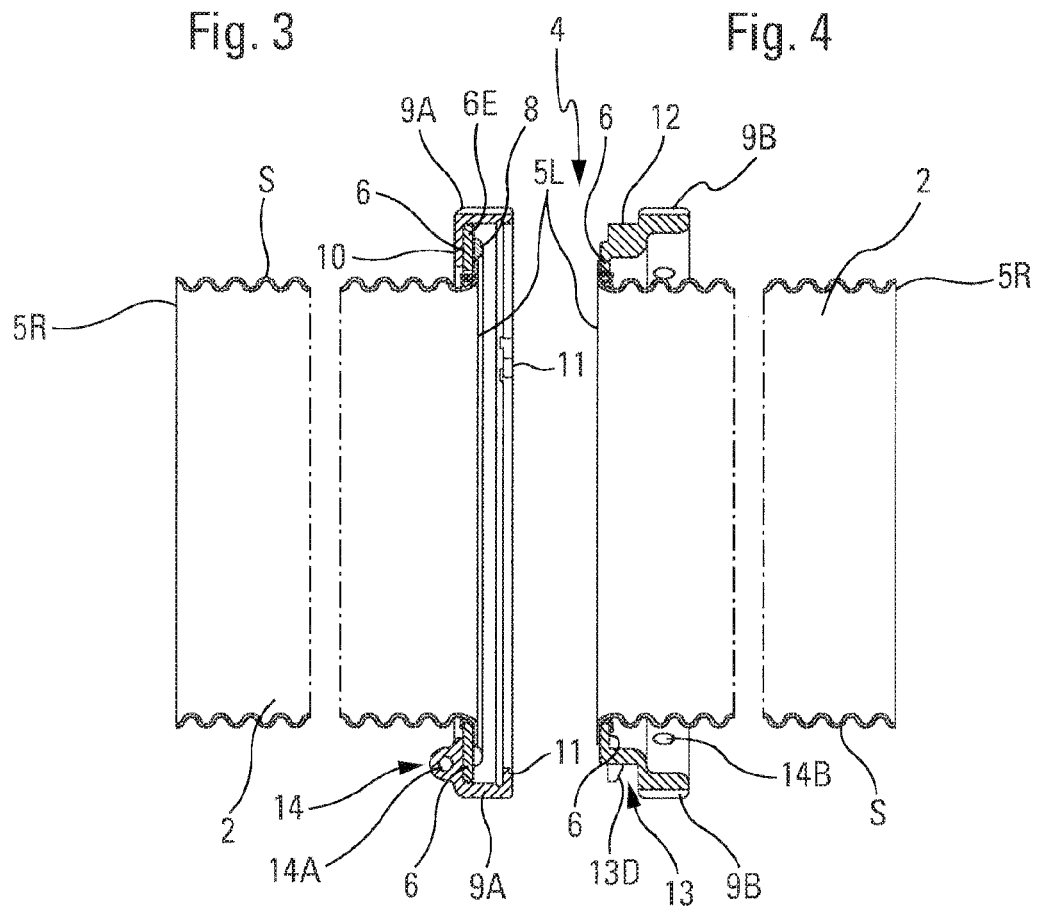
FIG. 5 is a diagrammatic view in longitudinal cross-section of the prosthesis according to the invention along the cutting line V-V of FIGS. 3 and 4, when the two individual tubular elements of the prosthesis are not connected to each other.
Figure 6:
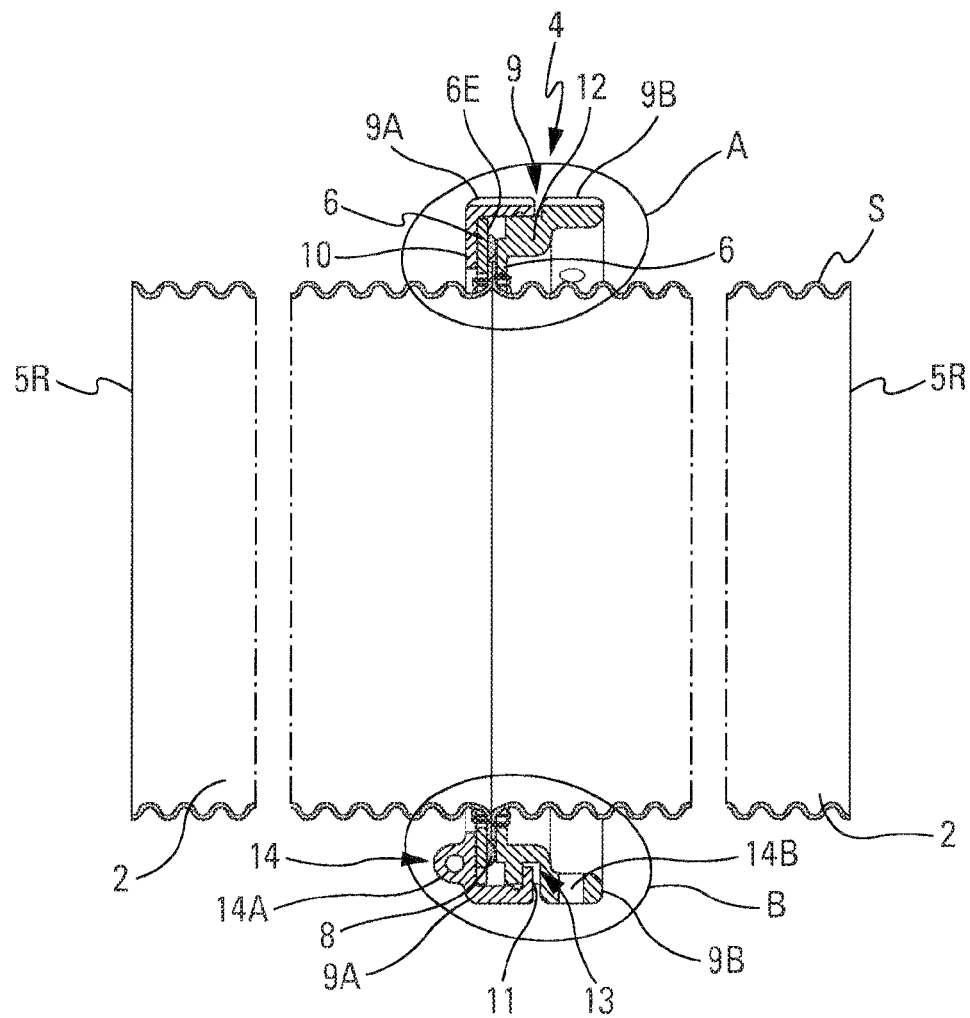
FIG. 6 is similar to FIG. 5 except that the two individual tubular elements are now connected to each other.
Figure 7:
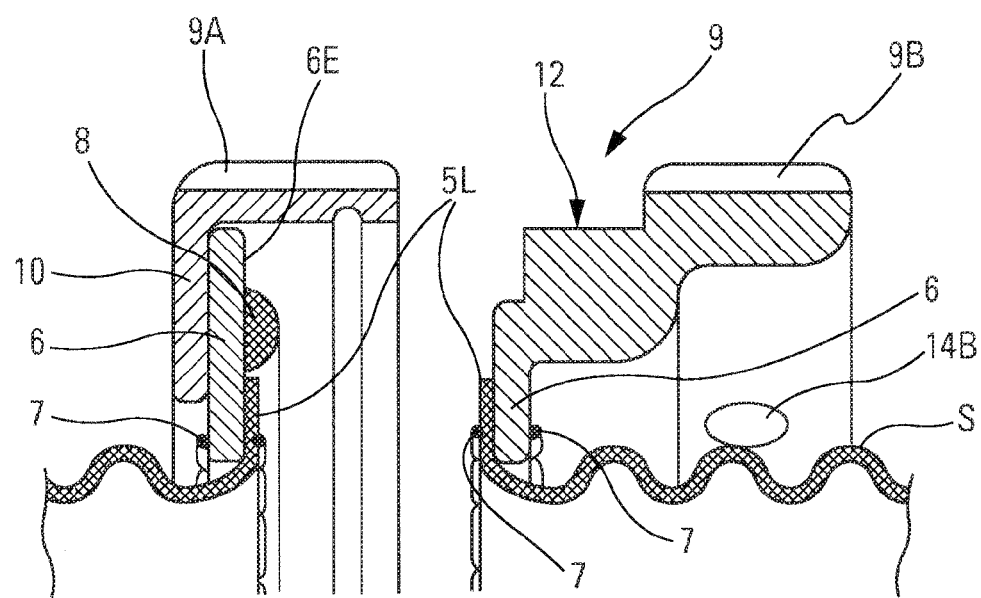
FIG. 7 shows diagrammatically an enlargement of zone A of FIG. 6 when the two individual tubular elements are not connected to each other.
Figure 8:
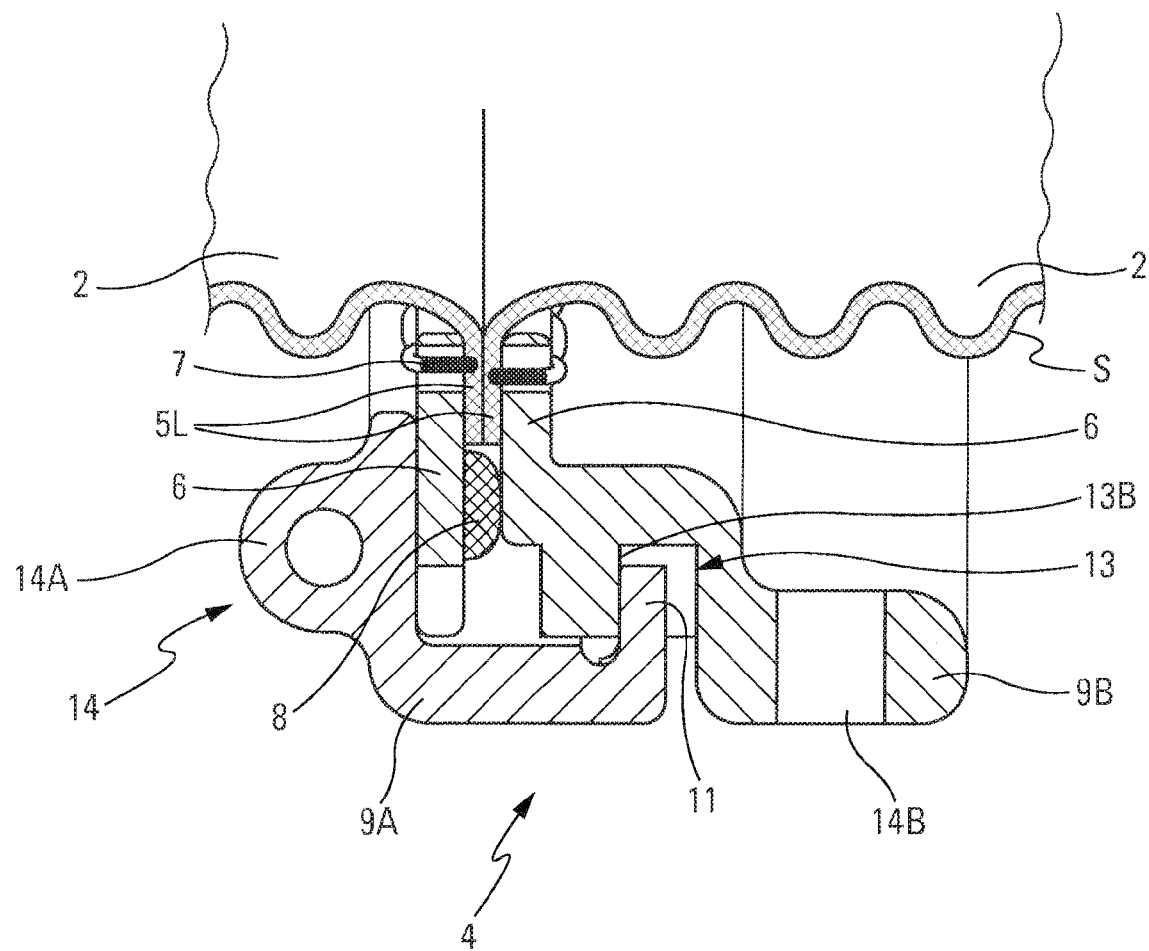
FIG. 8 is a diagrammatic enlargement of zone B of FIG. 6.

The tubular prosthesis 1 according to the present invention and illustrated in FIGS. 1 and 2, comprises two individual tubular elements 2, for example made of woven polyester, each defining an internal opening 3.

The individual cylindrical tubular elements 2 are designed to be sutured by a surgeon at one of their ends 5R to a portion P of an anatomical duct C to be treated.

The outer surface S of each of the individual tubular elements 2 is annulate so as to be flexible and provide better engagement in the corresponding portion P of the anatomical duct C.

The prosthesis 1 also comprises sealed mechanical means 4 for connecting the respective free ends 5L of the two individual tubular elements 2 (the free ends 5L being those that are not sutured to the portions P).

As shown in FIGS. 3 to 8, the mechanical connection means 4 comprise:
  two annulus-shaped joining parts 6 which are fixed respectively to a free end 5L of an individual tubular element 2. Each tubular element 2 can be fixed to an annulus 6 by gluing and/or by suturing 7 its free end 5L thereto (it being possible for the suture to be made leak-proof during the manufacturing process of the prosthesis 1). In particular, each tubular element 2 passes through the internal opening of the corresponding annulus 6 in order to cover, with its free end 5L, at least a portion of the outer surface 6E (i.e. that turned towards the other tubular element 2) thereof.
  an annular seal 8 which is positively connected with the outer surface 6E of the annulus 6 and which is positioned in the vicinity of the opening 3. The seal 8 is designed to be compressed by the two annuluses 6 when the corresponding two individual tubular elements 2 are connected to each other; and
  mechanical means 9 for holding the annuluses 6 against each other while compressing the seal 8 between them in order to seal the length of the tubular prosthesis 1.

The holding means 9 comprise a first 9A and a second 9B fixing ring which are designed to cooperate with each other and which are each traversed by the associated tubular element 2.

In this example, the first ring 9A comprises an inner flange 10 on which a corresponding annulus 6 can be firmly pressed.

It also comprises projections 11 in the form of a stud which extend radially towards the inside of the ring 9A.

The second ring 9B comprises a projecting annular collar 12 at the end of which the other annulus 6 is positively connected. Advantageously, the ring 9B, the collar 12 and the associated annulus 6 can be formed as one and the same part.

The projecting collar 12 is suitable for being inserted, with adjustment, inside the first ring 9A. In this way, the annulus 6, which is positively connected with the projecting collar 12, is pressed firmly against the seal 8 carried by the annulus 6 of the ring 9B.

Furthermore, the collar 12 comprises recesses 13 which are made in the side wall thereof and which are suitable for receiving the corresponding radial projections 11.

Each recess 13 comprises:
  an axial notch 13A oriented outwards and suitable for receiving one of the studs 11; and
  a locking incline 13B extending over a specified angular sector, the entrance of which consists of an associated axial notch 13A.

In particular, each locking incline 13B may be helical so as to end in a locking notch 13C, which allows the seal to be compressed in a pre-determined manner when the corresponding stud 11 has reached the locking notch 130 while immobilising the two rings 9A and 9B relative to each other in a locked position.

In the example described, the first ring 9A comprises three studs 11 and consequently the collar 12 comprises three associated recesses 13 to receive the corresponding studs 11.

The studs 11 and the corresponding recesses 13 are advantageously distributed at equal angles to maintain uniform compression along the seal 8.

In addition, to further secure the immobilisation of the two rings relative to each other, the prosthesis 1 comprises auxiliary fixing means 14.

In the example described, the auxiliary fixing means 14 are in the form of fixing eyelets 14A positively connected with the first fixing ring 9A, to which fixing orifices 14B made in the side wall of the second fixing ring 9B, open at the bottom, are respectively associated.

To immobilise the two rings 9A and 9B relative to each other in the locked position, suture thread 15 (see FIG. 2) for example may be used, in order to connect each eyelet 14A to the corresponding fixing orifice 14B to ensure that the rings 9A and 9B do not rotate relative to each other.

Each eyelet 14A is mounted on the first ring 9A in a longitudinal extension of a stud 11. Furthermore, each fixing orifice 14B is made in a longitudinal extension of a locking notch 13C.

Therefore, when the studs 11 engage with the notch 13C of the recesses 13, the eyelets 14A are aligned longitudinally with the corresponding fixing orifices 14B (see in particular FIG. 2).

Moreover, it goes without saying that the present invention is not limited to the embodiment of the mechanical connection means described above.

The invention claimed is:
1. Tubular prosthesis for connecting an anatomical duct, which comprises:
  at least two individual tubular elements and
  mechanical means for connecting said individual elements to each other, wherein the mechanical connecting means are sealed and comprise:
    two annulus-shaped joining parts each of them being fixed to the free end of an individual tubular element;

at least one seal carried by one of the two joining parts and designed to be inserted between the two joining parts around the opening formed by the tubular prosthesis; and a first and a second fixing ring each traversed by an individual tubular element and designed to cooperate with each other to hold together, one against the other, the two joining parts between which the seal is compressed; wherein each of the two tubular elements respectively contacts and covers with the free end thereof at least a portion of an outer surface of a respective one of the two joining parts, said outer surface being turned toward one of the tubular elements.

2. Prosthesis according to claim 1, wherein:

the first fixing ring comprises an inner flange on which one of the annuluses is designed to be firmly pressed;

the second fixing ring comprises a projecting annular collar at the end of which the other annulus is positively connected; and the projecting collar is suitable for being inserted inside the first ring in order to put the two annuluses in contact with each other.

3. Prosthesis according to claim 2, wherein:

the first fixing ring comprises internal radial projections; and the second fixing ring comprises recesses made in the side wall of the projecting collar and which are suitable for receiving the corresponding radial projections of the first ring.

4. Prosthesis according to claim 3, wherein:

each of the radial projections is in the form of a stud; and each of the recesses comprises:

an axial notch for the insertion of a radial projection; and a locking incline extending over a particular angular sector, the entrance of which is formed by an associated axial notch.

5. Prosthesis according to claim 4, wherein the locking incline is helical and ends in a locking notch.

6. Prosthesis according to claim 3, wherein the radial projections and the corresponding recesses are distributed at equal angles.

7. Prosthesis according to claim 1, wherein auxiliary fixing means are provided for holding said annuluses securely against each other.

8. Prosthesis according to claim 7, wherein said auxiliary fixing means comprise at least one fixing eyelet positively connected to the first fixing ring, and at least one corresponding fixing orifice made in the side wall of the second fixing ring.

9. Prosthesis according to claim 1, wherein the two tubular elements respectively abut against one another at the respective free ends thereof in non-telescoping fashion.

10. Prosthesis according to claim 1, wherein the two tubular elements respectively abut against one another at the respective free ends thereof by a longitudinal compressive force.

* * * * *